United States Patent [19]

Panzer et al.

[11] 4,157,442
[45] Jun. 5, 1979

[54] PROCESS FOR PREPARATION OF 2-VINYLTETRAHYDROPYRIMIDINES

[75] Inventors: Hans P. Panzer, Stamford; Kenny U. Acholonu, Bridgeport, both of Conn.

[73] Assignee: American Cyanamid Company, Stamford, Conn.

[21] Appl. No.: 867,065

[22] Filed: Jan. 5, 1978

[51] Int. Cl.² .............................................. C07D 233/06
[52] U.S. Cl. .................................................... 544/242
[58] Field of Search ...................... 260/251 R; 544/242

[56] References Cited

U.S. PATENT DOCUMENTS

| 2,921,964 | 1/1960 | Ramsden | 260/251 R |
| 3,179,668 | 4/1965 | Schickh et al. | 260/251 R |
| 3,919,225 | 11/1975 | Arnold et al. | 260/251 R |
| 4,039,542 | 8/1977 | Panzer et al. | 260/251 R |
| 4,044,009 | 8/1977 | Panzer et al. | 260/251 R |
| 4,074,055 | 2/1978 | Panzer et al. | 260/251 R |

*Primary Examiner*—Nicholas S. Rizzo
*Attorney, Agent, or Firm*—William J. van Loo

[57] ABSTRACT

2-vinyl-2-tetrahydropyrimidines are prepared by cleaving 2-acylamidoethyl-2-tetrahydropyrimides at suitable temperature distilling the cleavage products, and recovering the desired product from the distillate.

5 Claims, No Drawings

PROCESS FOR PREPARATION OF 2-VINYLTETRAHYDROPYRIMIDINES

CROSS-REFERENCE TO RELATED APPLICATIONS:

This application is related to applications Ser. Nos. 867,252 and 867,249, filed on even date herewith. The instant application relates to preparation of 2-vinyl-2-pyrimidines. Ser. No. 867,252 relates to 2-acylamidoethyl-2-tetrahydropyrimides which are cleaved in the present application and Ser. No. 867,249 relates to a process for preparing 2-acylamidoethyl-2-tetrahydropyrimidines.

This invention relates to a process for preparing 2-vinyl-2-tetrahydropyrimidines. More particularly, this invention relates to such a process wherein a 2-acylamidoethyl-2-tetrahydroimidazoline is cleaved to provide the desired 2-vinyl-2-tetrahydropyrimidine.

The need for high efficiency products for use in the treatment of aqueous suspensions of solids has continued to grow in recent years because of the increasing awareness of the environment pollution caused by such substances and other considerations. Accordingly, there have been increased efforts expended in attempts to provide such products which can be used to facilitate the dewatering of aqueous suspensions or organic, or mixtures of organic and inorganic materials, such as distillery wastes, fermentation wastes, wastes from paper manufacturing plants, dye plant wastes, and sewage suspensions such as digested sludges, activated sludges, or raw and primary sludges from sewage treatment plants as well as a host of other suspension types.

The more recent and more successful materials used in the treatment of such suspensions have been amidine or imidazoline polymers, see U.S. Pat. Nos. 3,406,139; 3,450,646; 3,576,740 and 3,666,705. Such polymers are very effective materials for use in the treatment of industrial wastes. The polymers are produced, however, by the treatment of corresponding nitrile polymers and are therefore governed by the structure of the nitrile polymers. Furthermore, conversion of the nitrile polymers to the imidazoline or amidine form does not reach 100% and therefore a portion of the resultant polymer is in improper form to function in water treating capacity.

Prior attempts to obviate these difficulties have included rearrangement of the groups present in the nitrile charge polymer and the attempted production of unsaturated imidazolines and amides which may be homopolymerized or copolymerized into more active imidazoline and amidine polymers. However, attempts to produce intermediates, from which the unsaturated imidazolines and amidines may be prepared have proven unsuccessful. Furthermore, attempts to follow the teachings of U.S. Pat. No. 3,210,371 resulted only in the production of undesired polymeric material and the teachings of Oxley et al., J. Chem. Soc. 1947, page 497–505, also resulted in the recovery of undesired polymeric products. Recent developments are typified by U.S. Pat. Nos. 4,006,247 and 4,007,200. In U.S. Pat. No. 4,007,200, there are disclosed intermediates which require numerous preparative steps which are difficult to perform, thus complicating processing and reducing yields of the intermediate. In U.S. Pat. No. 4,006,247, it is disclosed that the intermediates of U.S. Pat. No. 4,007,200 can be cracked to provide unsaturated imidazolines and amidines. However, the intermediate is unstable in cracking, thus reducing yields of unsaturated compounds. The cracking process is difficult to perform and undesirable.

There continues to exist the need for a process for preparing unsaturated pyrimidines which is readily conducted while avoiding the deficiencies of the former processes. Such a provision would fulfill a long-felt need and constitute a notable advance in the art.

In accordance with the present invention, there is provided a process for preparing compounds of the structure:

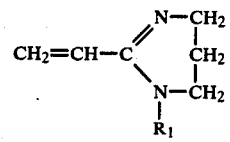

wherein $R_1$ is hydrogen or an alkyl group of about 1 to 5 carbon atoms, said process comprising heating to cracking temperature a compound of the structure:

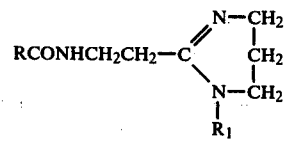

wherein R is an alkyl group of about 1 to 5 carbon atoms and $R_1$ is hydrogen or an alkyl of about 1 to 5 carbon atoms, distilling the cleavage products, and recovering the desired compound from the distillate.

The process of the present invention provides 2-vinyl-2-tetrahydropyrimidines in monomer form which can be readily processed to the desired polymers for the various uses previously mentioned. The present process employs stable intermediates which enable the desired vinylpyrimidine monomers to be distilled from the reaction vessel under vacuum.

In carrying out the process of the present invention, the starting intermediate is a 2-acylamidoethyl-2-tetrahydropyrimidine of the structure:

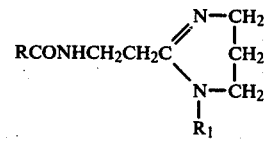

wherein R is an alkyl group of about 1 to 5 carbon atoms and $R_1$ is hydrogen or an alkyl of about 1 to 5 carbon atoms. The 2-acylamidoethyl-2-tetrahydropyrimidines are readily prepared by reacting a 2-cyanoethylacylamide with a suitable propylenediamine in equal molar proportions under conditions such that one molar equivalent of $NH_3$ is evolved and ring closure results. The 2-cyanoethylacylamides are well-known in the art and are obtained by reacting an acylamide with acrylonitrile in the presence of a strong alkali. The reaction is described in the Chemistry of Acrylonitrile, IV Cyanoethylation of Active Hydrogen Groups, Bruson and Riener, J. Am. Chem. Soc., 65, page 23 (1943). This reaction is given by the equation

For purposes of this invention R is an alkyl group of about 1 to 5 carbon atoms.

Using a selected 2-cyanoethylacylamide as described, the desired 2-acylamidoethyl-2-imidazoline is prepared by reaction with a propylenediamine of the structure $R_1HNCH_2CH_2CH_2NH_2$ wherein $R_1$ is hydrogen or an alkyl group of about 1 to 5 carbon atoms, preferably in the presence of a suitable catalyst. A preferred catalyst is sulfur. The reaction is carried out at an elevated temperature to minimize reaction time but at a temperature safely below that at which decomposition occurs. Reaction is quite rapid, generally 90 minutes or less at 115° C. A solvent may be used if desired but reaction can be effected in the absence of solvent. The crude product is readily purified by recrystallization, for example, and yields of pure product are 70% or higher. The reaction follows the equation

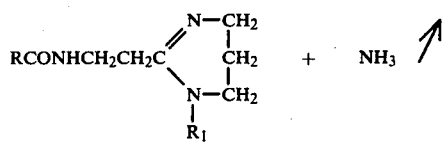

The reactants are generally employed in equal molar amounts. If a catalyst is employed, it is used in effective amount. Preferably, sulfur is used at a concentration of about 0.5 to 1.0 weight percent based on the weight of reactants. As indicated, a solvent may be used if desired and, if used, should generally be in an amount providing suitable fluidity to the reaction mixture. A preferred solvent is toluene.

2-acylamidoethyl-2-tetrahydropyrimidines are readily cleaved according to the present invention to 2-vinyl-2-tetrahydropyrimidines. In carrying out the process of the present invention, the 2-acylamidoethyl-2-pyrimidine is one having the general structure:

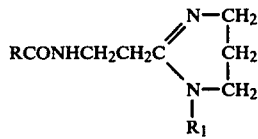

wherein R is an alkyl group of about 1 to 5 carbon atoms and $R_1$ is hydrogen or an alkyl group of about 1 to 5 carbon atoms.

The selected 2-acylamidoethyl-2-pyrimidine is heated to cracking temperature to provide a 2-vinyl-2-tetrahydropyrimide and an acylamide according to the reaction

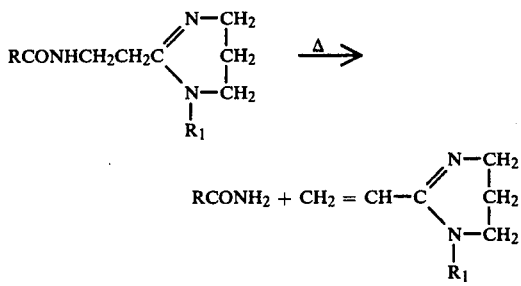

The cleavage products are distilled and since the 2-vinyl-2-pyrimidine has a lower boiling temperature than the acylamide, it constitutes a major fraction of the distillate. The distillate is collected and the desired 2-vinyl-2-tetrahydropyrimidine is recovered from the distillate, generally as a suitable salt.

The invention is more fully illustrated by the examples which follow wherein all parts and percentages are by weight unless otherwise specified.

INTERMEDIATE PREPARATION

Preparation of 2-Acetamidoethyl-2-tetrahydropyrimidine

To a 500 ml round-bottomed flask equipped with a thermometer and reflux condenser were added 129.00 grams (1.15 mol) of 2-cyanoethylacetamide, 83.62 grams (1.13 mol) of 1,3-diaminopropane, 1.5 grams of sulfur and 100 ml. of toluene as solvent. The reaction mixture was heated to 110° C. and held at this temperature for 3 hours. A solid product precipitates upon cooling in the amount of 186 grams. Upon recrystallization of the crude product from ethylether-ethanol (150 ml. 1:3), 149 grams of pure product was recovered representing a yield of 78.5%. The product had a melting point of 165°–167° C.

EXAMPLE 1

To a 250 ml. round-buttomed flask equipped with a distillation head, vacuum take-off adapter, and a receiver were added 22.2 grams (0.144 mol) of 2-acetamidoethyl-2-tetrahydropyrimidine as obtained in Example 1, 11.5 grams of Celite, 4.0 grams of potassium hydroxide, 4.8 milligrams of Cupferon, and 0.5 gram of phenothiazine. The mixture was thoroughly mixed and heated to 200° C. at a pressure equivalent to 0–5 millimeters of mercury. The yield of 2-vinyl-2-tetrahydropyrimidine was 50% based on NMR.

EXAMPLES 2–5

Following the procedure of Example 1, the following 2-acetamidoethyl-2-tetrahydropyrimidines were successfully cracked. The compounds and example numbers are listed below.

| Example No. | 2-Acylamidoethyl-2-tetrahydropyrimidine | |
|---|---|---|
| | R - Group | $R_1$ Group |
| 2 | $C_2H_5-$ | $H-$ |
| 3 | $C_3H_7-$ | $CH_3-$ |
| 4 | $C_2H_5-$ | $C_2H_5-$ |
| 5 | $CH_3-$ | $C_3H_7-$ |

We claim:

1. A process for preparing compounds of the structure

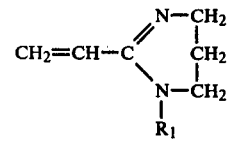

wherein $R_1$ is hydrogen or an alkyl group of about 1 to 5 carbon atoms, said process comprising heating to cracking temperature a compound of the structure

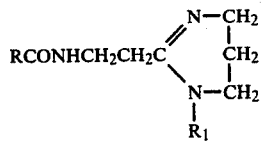

wherein R is an alkyl group of about 1 to 5 carbon atoms and $R_1$ is hydrogen or an alkyl group of about 1 to 5 carbon atoms, distilling the cleavage products, and recovering the desired compound from the distillate.

2. The process of claim 1 wherein R is methyl and $R_1$ is hydrogen.

3. The process of claim 1 wherein R is ethyl and $R_1$ is hydrogen.

4. The process of claim 1 wherein R is propyl and $R_1$ is methyl.

5. The process of claim 1 wherein R is ethyl and $R_1$ is ethyl.

* * * * *